(12) United States Patent
Jegou

(10) Patent No.: US 12,138,338 B2
(45) Date of Patent: Nov. 12, 2024

(54) PROCESS FOR TREATING KERATIN FIBRES WITH A PHOTOCROSSLINKABLE POLYVINYL ALCOHOL

(71) Applicant: L'OREAL, Paris (FR)

(72) Inventor: Gwenaëlle Jegou, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/466,738

(22) PCT Filed: Dec. 20, 2017

(86) PCT No.: PCT/EP2017/083799
§ 371 (c)(1),
(2) Date: Jun. 5, 2019

(87) PCT Pub. No.: WO2018/115113
PCT Pub. Date: Jun. 28, 2018

(65) Prior Publication Data
US 2019/0343754 A1    Nov. 14, 2019

(30) Foreign Application Priority Data

Dec. 21, 2016   (FR) ...................................... 1663052

(51) Int. Cl.
| A61K 8/81 | (2006.01) |
| A61Q 5/06 | (2006.01) |
| C08F 8/28 | (2006.01) |
| C08F 8/30 | (2006.01) |
| C08F 8/48 | (2006.01) |
| C08F 216/06 | (2006.01) |

(52) U.S. Cl.
CPC .............. *A61K 8/8129* (2013.01); *A61Q 5/06* (2013.01); *C08F 8/28* (2013.01); *C08F 8/30* (2013.01); *C08F 8/48* (2013.01); *C08F 216/06* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| 4,272,620 | A | 6/1981 | Ichimura |
| 4,287,335 | A | 9/1981 | Ichimura |
| 4,339,524 | A | 7/1982 | Ichimura et al. |
| 4,564,580 | A | 1/1986 | Ichimura et al. |
| 4,777,114 | A | 10/1988 | Ichimura et al. |
| 5,206,113 | A | 4/1993 | Mueller-Hess et al. |
| 8,609,074 | B2 | 12/2013 | Bui et al. |
| 2003/0022104 | A1 | 1/2003 | Takano et al. |
| 2005/0227166 | A1 | 10/2005 | Chimura et al. |
| 2006/0154187 | A1* | 7/2006 | Wilson .................... G03F 7/322 430/331 |
| 2006/0239946 | A1 | 10/2006 | Samain et al. |
| 2013/0167859 | A1 | 7/2013 | Bui et al. |

FOREIGN PATENT DOCUMENTS

WO    2016/174041 A1    11/2016

OTHER PUBLICATIONS

Yang et al., Huadong Fangzhi Gonfxueyan Xuebao, 12(1) p. 79-85, 1986 CAPLUS abstract (Year: 1986).*
Glosary: Ultraviolet radiation from https://ec.europa.eu/health/scientific_committees/opinions_layman/glossary/tuv/uv-radiation.htm, accessed Sep. 14, 2020 (Year: 2020).*
International Search Report and Written Opinion for Application No. PCTEP2017083799, mailed Mar. 12, 2018.
Non-Final Office Action for U.S. Appl. No. 13/341,875, dated Feb. 14, 2014 (now abandoned).
Final Office Action for U.S. Appl. No. 13/341,875, dated Oct. 6, 2014 (now abandoned).
Non-Final Office Action for U.S. Appl. No. 13/341,875, dated Mar. 17, 2016 (now abandoned).
Final Office Action for U.S. Appl. No. 13/341,875, dated Sep. 6, 2016 (now abandoned).
Non-Final Office Action for U.S. Appl. No. 13/341,875, dated Jun. 28, 2018 (now abandoned).
Non-Final Office Action for U.S. Appl. No. 16/202,748, dated Dec. 31, 2018 (now abandoned).
Final Office Action for U.S. Appl. No. 16/202,748, dated Aug. 1, 2019 (now abandoned).

* cited by examiner

Primary Examiner — Nissa M Westerberg
(74) Attorney, Agent, or Firm — THE MARBURY LAW GROUP, PLLC

(57) ABSTRACT

The invention relates to a cosmetic process for treating keratin fibres, comprising: (i) a step of applying to the keratin fibres a cosmetic composition containing a polyvinyl alcohol polymer comprising:—an alcohol unit—optionally an acetate unit—a photocrosslinkable unit—a hydrophobic unit; (ii) a step of irradiating the composition on the keratin fibres to crosslink said polymer. The invention also relates to the novel polyvinyl alcohol polymer used in said process. The treated keratin fibres have good cosmetic properties in terms of a soft feel and disentangling, which properties are persistent after one or more shampoo washes.

20 Claims, No Drawings

PROCESS FOR TREATING KERATIN FIBRES WITH A PHOTOCROSSLINKABLE POLYVINYL ALCOHOL

CROSS REFERENCE TO RELATED APPLICATION

This is a national stage application of PCT/EP2017/083799, filed internationally on Dec. 20, 2017, which claims priority to French Application No. 1663052, filed on Dec. 21, 2016, both of which are incorporated by reference herein in their entireties.

The present invention relates to a process for the cosmetic treatment of keratin fibres using a polyvinyl alcohol polymer bearing photocrosslinkable and hydrophobic groups, and also to novel polymers.

Hair products generally contain film-forming polymers to give the hair good hairstyle hold. However, the quality of the hair hold may be impaired on contact with water, for example with rain or when showering: this impairment may be due to the fact that the deposit of the film-forming polymer on the hair has poor resistance to contact with water and is removed over time.

The aim of the present invention is to provide a process for the cosmetic treatment of the hair which can produce a film-forming deposit that has good resistance to water and that is suitable for application to the hair to obtain good cosmetic properties in terms of a soft feel and disentangling, which properties are persistent after shampoo washing one or more times (for example 5 times).

In the field of electronics and recording equipment, photosensitive resins comprising photodimerizable units and hydrophobic units have been developed (U.S. Pat. Nos. 4,777,114, 5,206,113 and US 2003/0022104).

Other photodimerizable polymers have been used in cosmetics (US2006/0239946, WO 2016/174041, US 2013/0167859 and US 2013/0167859).

However, the feel, disentangling and persistence especially on shampooing is not always satisfactory.

The inventors have discovered that a particular vinyl alcohol polymer applied to the hair gives the hair good cosmetic properties which show good persistence on shampooing.

More precisely, one subject of the present invention is a process, especially a cosmetic process, for treating keratin fibres, comprising:
  (i) a step of applying, to the keratin fibres, a cosmetic composition comprising a polyvinyl alcohol polymer as defined below;
  (ii) a step of irradiating the composition on the keratin fibres to crosslink said polymer;
  steps (i) and (ii) being performed at the same time or separately, in the order (i) and then (ii).

The polyvinyl alcohol polymer used according to the invention comprises:
  at least one alcohol unit of formula (I)
  optionally at least one acetate unit of formula (II)
  at least one photocrosslinkable unit of formula (P) and
  at least one hydrophobic unit of formula (H1) or (H2) below:

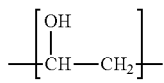

(I)

-continued

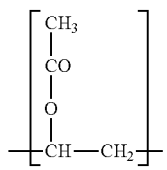

(II)

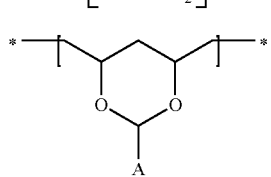

(H1)

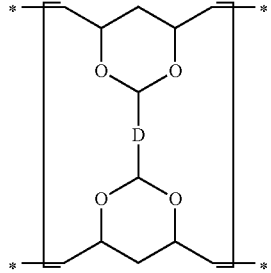

(H2)

(P)

in which:
A denotes a monovalent aromatic group of formula (A1) or (A2) below:

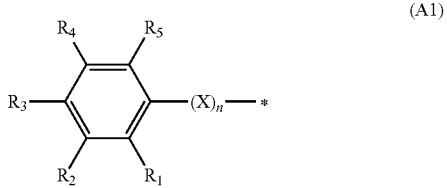

(A1)

in which R1, R2, R3, R4 and R5, which may be identical or different, denote H, OH, ORa, SRa, CO2H, —OCORb, —NRcRd, a C1-C4 alkyl radical optionally interrupted with one or more heteroatoms O, S or a divalent group N(Re), Ra denoting a C1-C6 alkyl group; Rb denoting a C1-C6 alkyl or benzyl group; Rc and Re denoting a C1-C4 alkyl group; Rd denoting H or a C1-C4 alkyl group;

one of the radicals R1, R2, R3, R4 or R5 also possibly denoting a group —O—K—Si(CH$_3$)$_3$, K denoting a divalent C2-C6 hydrocarbon-based group;
—N(CH$_2$CH$_2$OH)$_2$;

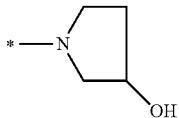
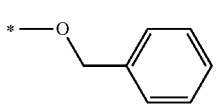

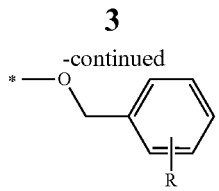

R denoting a C1-C6 alkyl radical or a C1-C4 alkoxy radical:

the group R3 also possibly denoting a —C(CH$_3$)=CH$_2$ radical n=0 or 1; preferably, n=0 (i.e. it denotes a covalent bond)

X denotes a divalent radical —CH=C(Rf)—, Rf denoting H or a C1-C6 alkyl radical;

with the proviso that when n=0, R1, R2, R3 and R4 do not simultaneously denote a hydrogen atom.

The proviso "when n=0, R1, R2, R3 and R4 do not simultaneously denote a hydrogen atom" means that R5 is as defined previously in the proviso, i.e. R5 represents in the proviso i) H, ii) OH, iii) ORa, iv) SRa, with Ra denoting a C1-C6 alkyl group, v) CO$_2$H, vi) —OCORb with Rb denoting a C1-C6 alkyl or benzyl group, vii) —NRcRd with Rc denoting a C1-C4 alkyl group and Rd denoting H or a C1-C4 alkyl group, viii) a C1-C4 alkyl radical, optionally interrupted with one or more heteroatoms O, S or a divalent group N(Re) with Re denoting a C1-C4 alkyl group; ix) —O—K—Si(CH$_3$)$_3$, K denoting a divalent C2-C6 hydrocarbon-based group; x) —N(CH$_2$CH$_2$OH)$_2$;

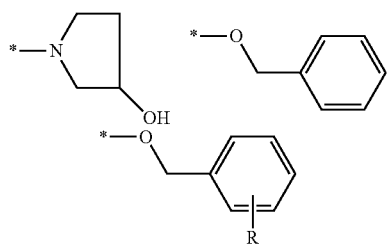

R denoting a C1-C6 alkyl radical or a C1-C4 alkoxy radical:

the group R3 also possibly denoting a —C(CH$_3$)=CH$_2$ radical n=0 or 1; preferably, n=0 (i.e. it denotes a covalent bond) X denotes a divalent radical —CH=C(Rf)— with Rf denoting H or a C1-C6 alkyl radical. In other words, A cannot represent the following group

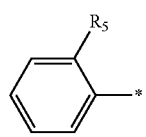

with R5 being as defined previously. The proviso "when n=0, R1, R2, R3 and R4 do not simultaneously denote a hydrogen atom" means that when n is 0, at least one group R1 to R5 is other than a hydrogen atom.

This is likewise the case for the other proviso "when n=0, one of the groups R1, R2, R3 or R4 denotes a methyl radical, the other groups denoting H", which means that R5 is as defined previously. In other words, A represents a group chosen from:

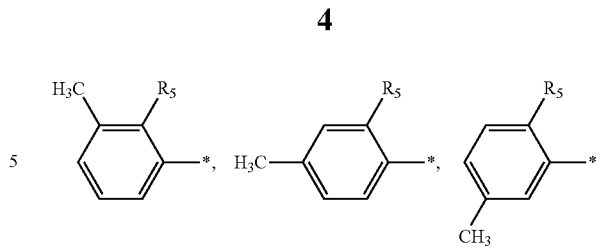

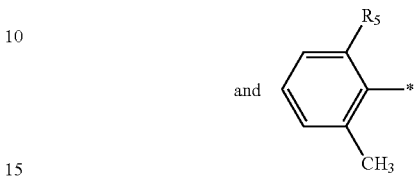

with R5 as defined previously, i.e. R5 represents i) H, ii) OH, iii) ORa, iv) SRa, with Ra denoting a C1-C6 alkyl group, v) CO$_2$H, vi) —OCORb with Rb denoting a C1-C6 alkyl or benzyl group, vii) —NRcRd with Rc denoting a C1-C4 alkyl group and Rd denoting H or a C1-C4 alkyl group, viii) a C1-C4 alkyl radical, optionally interrupted with one or more heteroatoms O, S or a divalent group N(Re) with Re denoting a C1-C4 alkyl group; ix) —O—K—Si(CH$_3$)$_3$, K denoting a divalent C2-C6 hydrocarbon-based group;

x) —N(CH$_2$CH$_2$OH)$_2$;

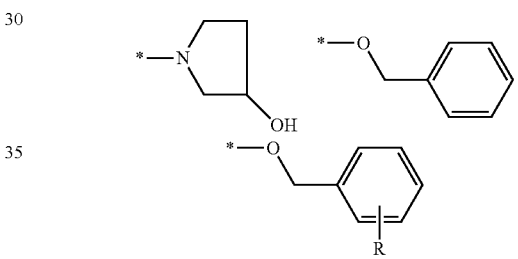

R denoting a C1-C6 alkyl radical or a C1-C4 alkoxy radical:

the group R3 also possibly denoting a —C(CH$_3$)=CH$_2$ radical n=0 or 1; preferably, n=0 (i.e. it denotes a covalent bond)

X denotes a divalent radical —CH=C(Rf)— with Rf denoting H or a C1-C6 alkyl radical.

Preferably, for formula (A1), R1, R2, R3, R4 and R5, which may be identical or different, denote H, OH, ORa, Ra denoting a C1-C3 alkyl group. Preferentially, R1, R2, R3, R4 and R5, which may be identical or different, denote H, OH, ORa, Ra denoting a C1-C3 alkyl group, and at least two, or even three, of the groups R1, R2, R3, R4 and R5 denote H.

(A2)

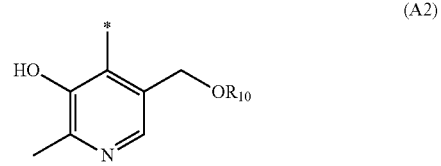

in which R$_{10}$ denotes H or a phosphate group —PO(OH)$_2$

D denotes a divalent group of formula (D1) or (D2) below:

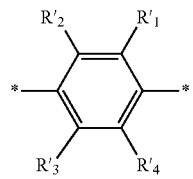
(D1)

in which R'1, R'2, R'3 and R'4, which may be identical or different, denote H, a C1-C4 alkyl radical, a C1-C4 alkoxy radical, one of the radicals R1, R2, R3 or R4 also possibly denoting a group NRgRh, Rg denoting H or a C1-C4 alkyl group, Rh denoting a C1-C4 alkyl group.

Preferably, for formula (D1), R'1, R'2, R'3 and R'4, which may be identical or different, denote H or a C1-C4 alkyl radical, especially a methyl radical.

Preferentially, R'1, R'2, R'3 and R'4, which may be identical or different, denote H or a C1-C4 alkyl radical, especially methyl.

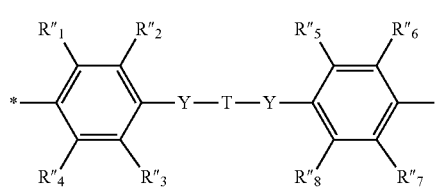
(D2)

in which R"1, R"2, R"3, R"4, R"5, R"6, R"7 and R"8, which may be identical or different, denote H, a C1-C4 alkyl radical or a C1-C4 alkoxy radical;

Y denotes O or —N(Rj)—, Rj denoting a C1-C4 alkyl group;

T denotes a divalent hydrocarbon-based group containing from 2 to 6 carbon atoms.

Q denotes a styrylpyridinium (stilbazolium, also known as SbQ) group of formula (Q1) or (Q2) below:

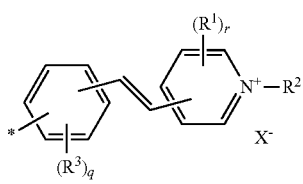
(Q1)

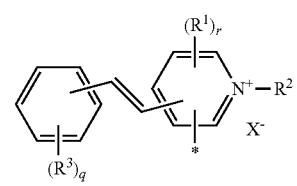
(Q2)

in which:
R¹ and R³, which may be identical or different, represent a halogen atom or a ($C_1$-$C_6$)alkyl group; or alternatively two contiguous groups R¹ or R³ form, together with the carbon atoms that bear them, a benzo group;

R² represents a hydrogen atom, a ($C_1$-$C_6$)alkyl group optionally substituted with one or more halogen atoms such as chlorine, or hydroxyl; preferably, R² represents a ($C_1$-$C_6$) alkyl group such as methyl, ethyl or propyl;

q and r represent an integer between 0 and 4 inclusive; and

X⁻ represents an anionic counterion preferably chosen from halide ions such as chlorides, bromides or iodides, perchlorates, tetrafluoroborates, methylsulfate, phosphates, sulfates, methanesulfonates or p-toluenesulfonate;

* represents the bond that connects the part of the monovalent radical to the rest of the polymer, it being understood that the side group $Q_2$ may be connected to the rest of the polymer via R²;

preferably the bond* is on the phenyl in the para position relative to the styryl group on $A_1$ or connected to the rest of the polymer via R² on $Q_2$; preferentially, the styryl group of $Q_1$ and $Q_2$ is para to the pyridinium group.

Preferably, the group Q represents a group bearing a stilbazolium function of formula (Ia):

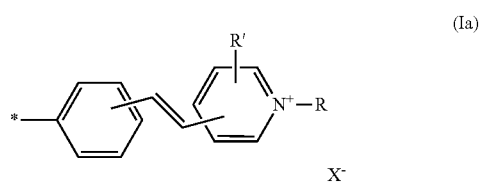
(Ia)

in which:
R represents a hydrogen atom or a $C_1$-$C_4$ alkyl or $C_1$-$C_4$ hydroxyalkyl group;
R' represents a hydrogen atom or a $C_1$-$C_4$ alkyl group, and
X⁻ denotes an anionic counterion preferably chosen from halide ions such as chlorides, bromides and iodides, perchlorates, tetrafluoroborates, methylsulfate, phosphates, sulfates, methanesulfonates, p-toluenesulfonate; preferably, the styryl group is para to the pyridinium group and/or para to the connecting bond ------*.

Preferentially, Q represents the group:

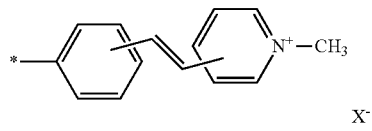

X⁻ being as defined previously, and preferably the methylsulfate or chloride anion.

In the chemical structures drawn, the * represents the bond connecting the part of the radical to the rest of the polymer.

Advantageously, the units of formula (II) may be present in the polyvinyl alcohol in a proportion ranging from 0.1 mol % to 40 mol % relative to the polymer, preferably ranging from 5 mol % to 20 mol %.

Advantageously, the polymer used according to the invention comprises a content of photocrosslinkable unit (P) ranging from 0.2 mol % to 10 mol %, preferably ranging from 0.5 mol % to 15 mol % and preferentially ranging from 0.5 mol % to 10 mol % relative to the polymer.

Advantageously, the polymer used according to the invention comprises a content of hydrophobic unit (H1) or (H2) ranging from 0.2 mol % to 50 mol %, preferably ranging from 0.5 mol % to 40 mol %, preferentially ranging from 0.5 mol % to 30 mol %, more preferentially ranging from 3 mol % to 25 mol % and better still ranging from 10 mol % to 25 mol % relative to the polymer.

The following scheme shows the crosslinking reaction which takes place between the photocrosslinkable groups such as the stilbazolium groups, under the effect of light, as illustrated below:

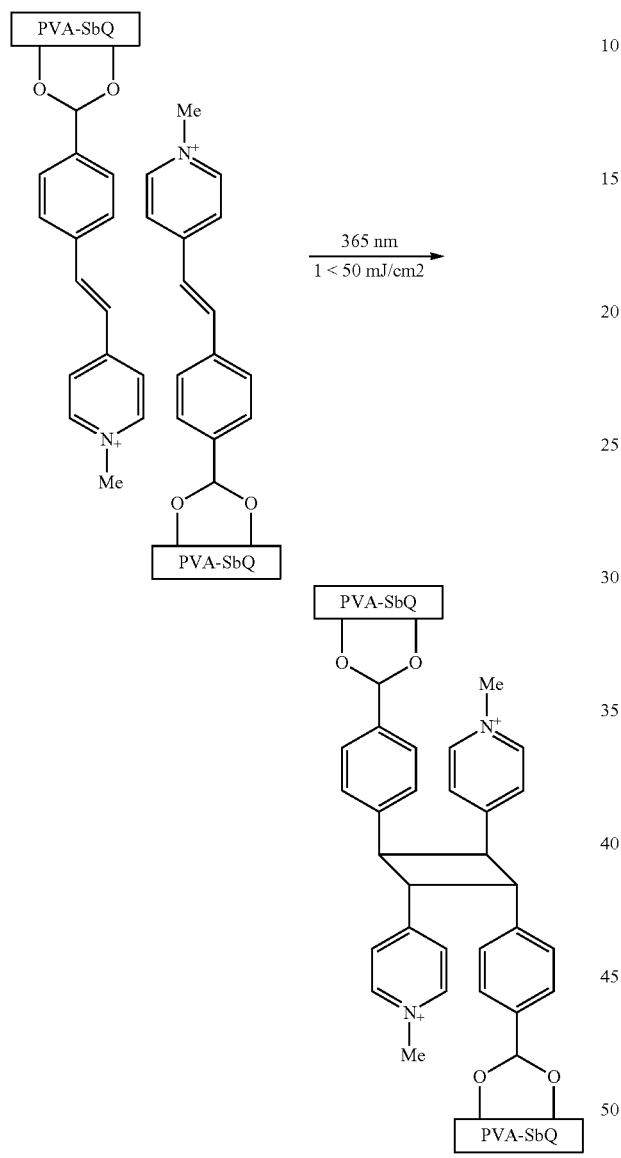

These materials are particularly appreciated since they do not require a photoinitiator and react with visible light or with radiation that may comprise both UV light and visible light, in particular a low dose of UV.

Preferably, the polymer used according to the invention has a weight-average molecular weight ranging from 10 000 to 200 000 g/mol.

The polymer used according to the invention may be prepared by reacting a polyvinyl alcohol with an aldehyde of formula A-CHO or a dialdehyde of formula OHC-D-CHO and an aldehyde of formula Q-CHO, the groups A, D and Q being as defined previously. The reaction may be performed in acidic aqueous medium (water or mixture of water and water-miscible solvents such as ethanol, isopropanol or butanol), especially at a temperature of between 25° C. and 85° C., especially for 1 to 12 hours.

As examples of hydrophobic monovalent groups (A1), mention may be made of the following groups:

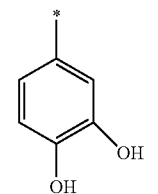

1

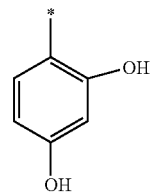

2

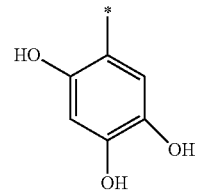

3

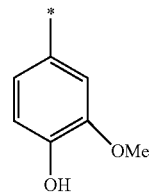

4

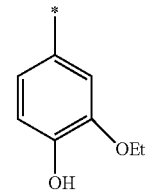

5

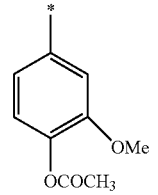

6

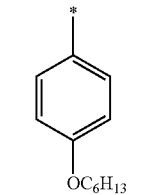

7

-continued
8
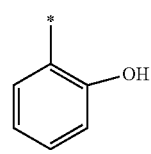
9
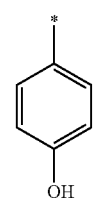
10
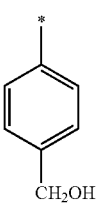
11
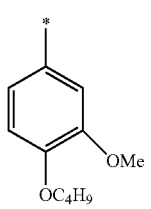
12
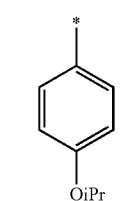
13
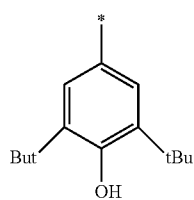
14
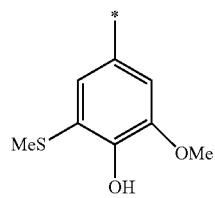
15
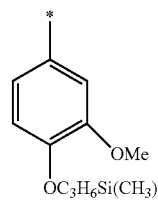
-continued
16
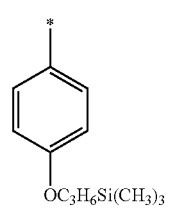
17
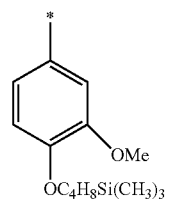
18
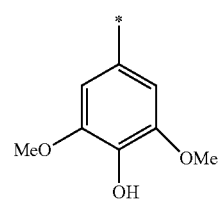
19
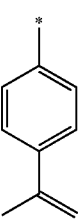
20
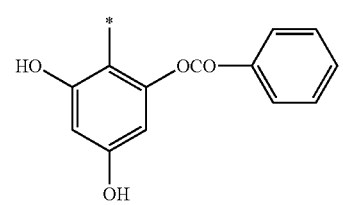
21
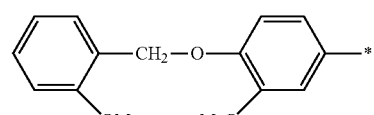
22
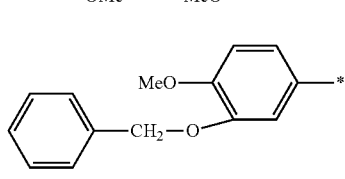
23
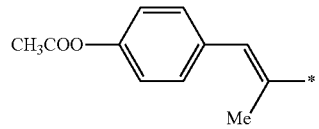
24
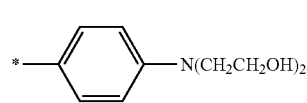

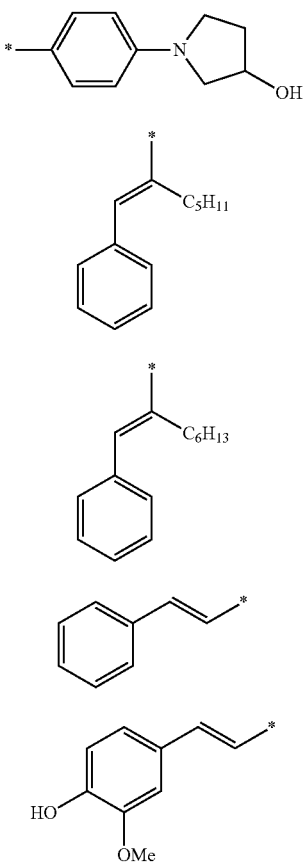

Preferably, (A1) is chosen from groups 1 to 5, 8 to 10, 12 and 18, preferentially from groups 1 to 5, 8, 9 and 18, and more preferentially from groups 1 and 4.

As examples of hydrophobic monovalent groups (A2), mention may be made of the following groups:

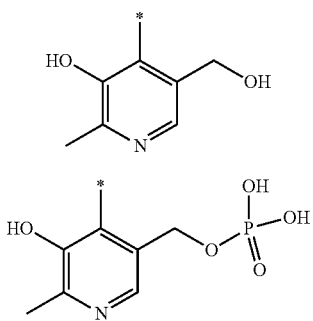

As examples of hydrophobic divalent groups (D1), mention may be made of the following groups:

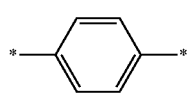

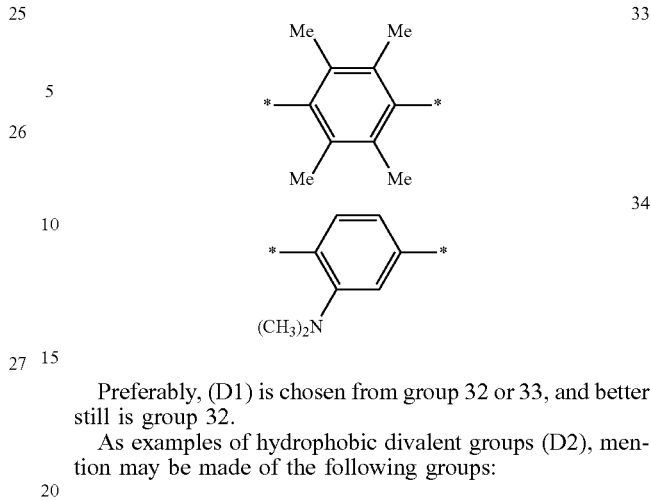

Preferably, (D1) is chosen from group 32 or 33, and better still is group 32.

As examples of hydrophobic divalent groups (D2), mention may be made of the following groups:

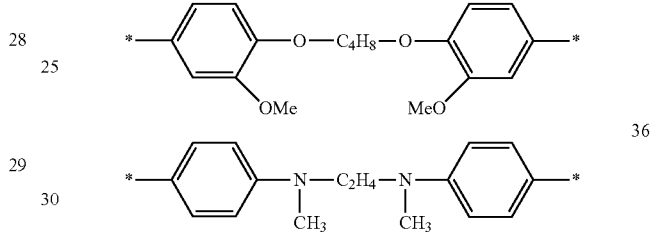

iPr=isopropyl
tBu=tert-butyl

Patent application US 2003/0022104 describes polyvinyl alcohol polymers bearing a group SbQ and bearing an aromatic group such as phenyl or methylphenyl.

A subject of the invention is also the novel polymers as described previously, with the proviso that, in the group of formula (A1), when n=0, R1, R2, R3 and R4 do not simultaneously denote a hydrogen atom and one of the groups R1, R2, R3 or R4 denotes a methyl radical, the other groups denoting H.

A subject of the invention is also a composition comprising, in a physiologically acceptable medium, a novel polymer as described previously.

The polymer used according to the invention may be used in a composition comprising a physiologically acceptable medium, in particular in a cosmetic composition.

The term "physiologically acceptable medium" means a medium that is compatible with human keratin fibres, in particular with the hair.

The term "cosmetic composition" means a composition that is compatible with keratin fibres, which has a pleasant colour, odour and feel and which does not cause any unacceptable discomfort (stinging, tautness or redness) liable to discourage the consumer from using it.

The polymer as defined previously may be present in the composition used according to the invention in a content ranging from 0.1% to 40% by weight, relative to the total weight of the composition derived from the extemporaneous mixing, preferably from 0.5% to 30% by weight, preferentially ranging from 1% to 20% by weight and more preferentially ranging from 1% to 10% by weight.

The process of the invention comprises a step ii) of irradiating the composition on the keratin fibres to crosslink the polymer.

This irradiation may consist of illumination, with ambient light or with a source of artificial light, of the composition applied to the keratin fibres.

The ambient or artificial light may emit radiation in the visible and/or UV range. Preferably, it emits at least a proportion of radiation in the UV range, for example a UV proportion of at least 2% of the total illuminating energy of the ambient light. According to a particular embodiment, the exposure comprises, or even consists of, illumination with ambient light of the treated hair, in particular for a time of at least 1 minute.

The exposure time to the ambient light may range more particularly from 10 seconds to 30 minutes and especially from 2 to 15 minutes.

According to another particular embodiment, the exposure comprises, or even consists of, illumination with a source of artificial light of the surface of said coat.

The exposure time to said artificial light may range from 1 second to 20 minutes and in particular from 1 second to 1 minute.

The crosslinking may take place with natural or artificial light, for example using lighting with a lamp, a flash, a laser or LEDs, for example in the form of an LED array.

The artificial light source may emit radiation in the visible range and/or radiation in the UV range.

The light emitted may or may not be monochromatic. The wavelength of the emitted light is preferably centred on 365 nm, in particular between 100 nm and 500 nm and better still between 200 nm and 420 nm.

Advantageously, the crosslinking is initiated by simple illumination without the need for a photoinitiator.

Preferably, it will be a source of artificial light emitting energy between 0.5 and 5 $W/cm^2$, the exposure times being adapted in consequence.

The crosslinking may occur with reduced light intensity, the lighting system may produce this light intensity for example between 500 $mJ/cm^2$ and 10 $J/cm^2$.

The twofold characteristic of the absence of a photoinitiator and the relatively low light intensity is particularly advantageous since it makes it possible to limit the harmful effects of aggressive initiators or of prolonged exposure to intense light, in particular in the UV wavelengths.

A person skilled in the art will be capable of adapting the illumination characteristics, especially in terms of exposure time and of radiation wavelengths, with regard to the nature of the photocrosslinkable polymer(s) (A) used. According to a preferred embodiment, the composition is applied to keratin fibres such as the hair.

According to this embodiment, the composition may be applied to wet or dry, clean or unclean keratin fibres. Preferably, the keratin fibres are dried after applying the composition and before irradiation.

It is also possible to include in the process, before or after the irradiation step ii), a pause at room temperature, or at elevated temperature, or under red light.

The process according to the invention may also comprise an additional step of drying the keratin fibres, after step (i) of applying the composition containing the polymer and before or after step (ii) of irradiating the keratin fibres. The drying step may be performed using a hairdryer or a drying hood or by drying naturally. The drying step is advantageously performed at a temperature ranging from 20 to 70° C.

After the irradiation step, the keratin fibres may be optionally rinsed with water or washed with a shampoo. The keratin fibres are then optionally dried using a hairdryer or a drying hood or dried naturally.

According to one embodiment, the process according to the invention is performed on natural or damaged or sensitized keratin fibres, which have optionally been dyed and/or have optionally undergone a prior long-lasting or temporary hair shaping treatment.

Damaged fibres are, for example, dry or coarse or brittle or split or soft fibres.

Sensitized fibres are, for example, bleached, relaxed or permanent-waved fibres.

The process according to the invention is preferably performed on dry keratin fibres, i.e. fibres that are not wet, especially dry hair.

After step (i) of applying to the keratin fibres the composition containing the polymer, and before performing step (ii) of irradiating the keratin fibres, the composition containing the applied polymer may be left on the fibres for a time ranging from 1 to 60 minutes, preferably ranging from 2 to 50 minutes and preferentially ranging from 5 to 45 minutes. The leave-on time may take place at a temperature ranging from 15° C. to 45° C., preferably at room temperature (25° C.).

The composition described previously is advantageously applied to the keratin fibres in an amount ranging from 0.1 to 10 grams and preferably from 0.2 to 5 grams of composition per gram of keratin fibres.

After application of the composition to the keratin fibres, they may be wrung out to remove the excess composition.

The treatment process according to the invention may be performed during and/or after, preferably after, an additional process of cosmetic treatment of the keratin fibres, such as a process for temporary hair shaping (hair shaping with curlers, a curling iron or a straightening iron) or a process for durable hair shaping (permanent-waving or relaxing) or a process for dyeing or bleaching the keratin fibres.

The treatment process according to the invention may also be performed as a post-treatment to a cosmetic treatment process.

In particular, the treatment process is performed as a post-treatment to a dyeing, bleaching, relaxing or straightening process and/or a permanent-waving process.

The composition used according to the invention is generally suitable for topical application to keratin fibres, and thus generally comprises a physiologically acceptable medium, i.e. a medium that is compatible with the skin and/or its integuments. It is preferably a cosmetically acceptable medium, i.e. a medium which has a pleasant colour, odour and feel and which does not cause any unacceptable discomfort (stinging, tautness or redness).

The cosmetic composition used according to the invention contains a physiologically acceptable medium, i.e. a medium that is compatible with human keratin materials such as the skin (of the body, face, eye contour or the scalp), the hair, the eyelashes, the eyebrows, bodily hair, the nails or the lips.

According to one embodiment of the invention, the cosmetic composition used according to the invention may comprise a physiologically acceptable aqueous medium. It may be constituted, for example, of water or of a mixture of water and of at least one cosmetically acceptable organic solvent. Examples of organic solvents that may be mentioned include $C_2$-$C_4$ lower alcohols, such as ethanol and isopropanol; polyols, especially those containing from 2 to 6 carbon atoms, for instance glycerol, propylene glycol, butylene glycol, pentylene glycol, hexylene glycol, dipropylene glycol or diethylene glycol; short esters such as ethyl acetate or butyl acetate; and mixtures thereof.

According to another embodiment of the invention, the cosmetic composition used according to the invention comprises a physiologically acceptable non-aqueous medium. It may be constituted, for example, of one or more cosmetically acceptable organic solvents, such as those described previously, or alternatively one or more common cosmetic oils.

The non-aqueous medium preferably comprises a volatile oil.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

These volatile oils may be hydrocarbon-based oils or silicone oils, or mixtures thereof. The term "hydrocarbon-based oil" means an oil mainly containing hydrogen and carbon atoms and possibly oxygen, nitrogen, sulfur and/or phosphorus atoms.

The volatile hydrocarbon-based oils may be chosen from hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names $^{Isopar}$® or Permethyl®.

Volatile silicone oils that may be mentioned include volatile linear or cyclic silicone oils, especially those with a viscosity 8 centistokes (cSt) ($8 \times 10^{-6}$ m²/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made in particular of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The compositions used according to the invention may also contain one or more cosmetic additives chosen from surfactants, sunscreens, fillers, colorants, nacreous agents, opacifiers, sequestrants, film-forming polymers, plasticizers, thickeners, oils, waxes, fragrances and preserving agents.

The compositions used according to the invention may be in any presentation form conventionally used and especially in the form of aqueous solutions, aqueous-alcoholic solutions, oil-in-water (O/W), water-in-oil (W/O) or multiple (triple: W/O/W or O/W/O) emulsions, aqueous gels or aqueous-alcoholic gels. These compositions are prepared according to the usual methods.

According to an advantageous embodiment of the invention the cosmetic composition used according to the invention comprises a mixture of water and protic polar solvent such as alcohols, especially $C_2$-$C_4$ lower alcohols, such as ethanol and isopropanol, preferably in equivalent amount such as 50/50, vol/vol.

The invention will now be described with reference to the examples that follow, which are given as non-limiting illustrations.

EXAMPLE 1

Polyvinyl Alcohol Polymer Functionalized with SbQ and Vanillin Groups (P1)

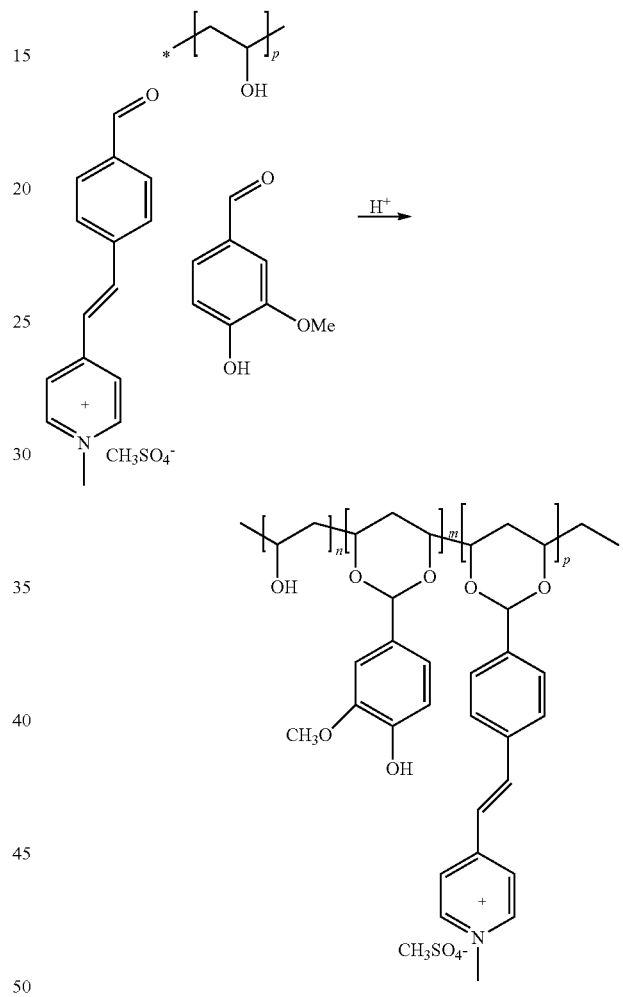

20 g of polyvinyl alcohol (Selvol® 540 from Sekisui) and 200 ml of a solvent mixture (50/50 weight/weight water/isopropanol) were placed in a reactor. The mixture was heated at 80° C. until dissolution of the polyvinyl alcohol was complete. 5 ml of 1M HCl and 1 g of vanillin and 1 g of N-methyl-4-(p-formylstyryl)pyridinium methyl sulfate (CA No. 74401-04-0) were then added. The reaction medium was maintained at 80° C. for 8 hours. The product was purified three times by precipitation from 600 ml of acetone. The purified product was placed in water/isopropanol aqueous-alcoholic solution (50/50 weight/weight) at 10% by weight of polymer (solution S1). The polymer obtained comprises 20% by weight of group derived from vanillin and 15% by weight of SbQ group derived from N-methyl-4-(p-formylstyryl)pyridinium methyl sulfate.

EXAMPLE 2

Polyvinyl Alcohol Polymer Functionalized with SbQ and 3,4-dihydroxybenzaldehyde Groups (P2)

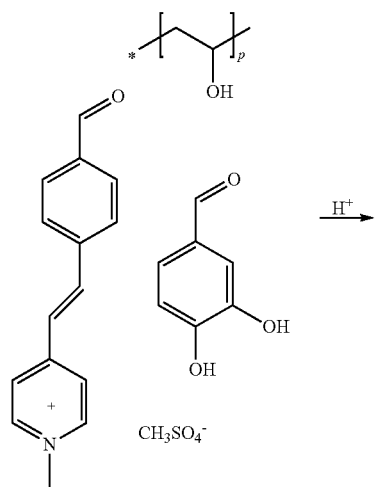

The polymer was prepared according to the procedure described in Example 1, using: 20 g of polyvinyl alcohol (Selvol 540 from Sekisui)

1 g of 3,4-dihydroxybenzaldehyde 1 g of N-methyl-4-(p-formylstyryl)pyridinium methyl sulfate Solvent: water/isopropanol (40/60 weight/weight): 200 ml The polymer obtained comprises 18% by weight of group derived from 3,4-dihydroxybenzaldehyde and 15% by weight of SbQ group derived from N-methyl-4-(p-formylstyryl)pyridinium methyl sulfate. After purification, the polymer was dissolved at 10% by weight in a water/isopropanol mixture (50/50 weight/weight).

A solution S2 of polymer 2 was thus obtained.

EXAMPLE 3

Polyvinyl Alcohol Polymer Functionalized with SbQ and Terephthaldehyde Groups (P3)

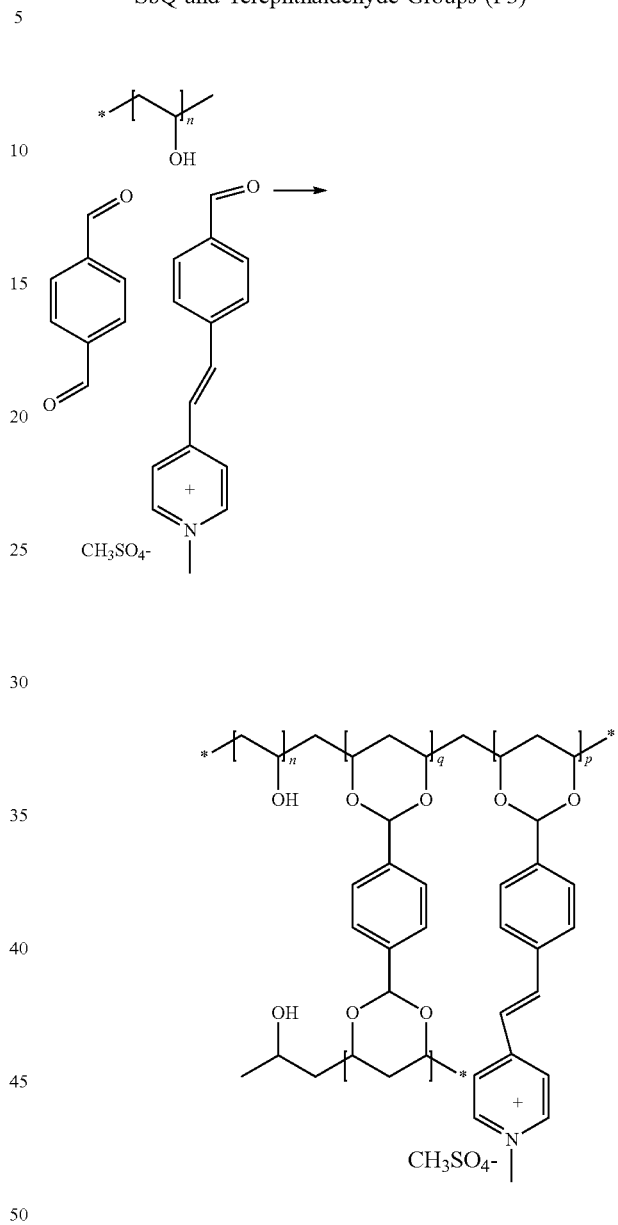

The polymer was prepared according to the procedure described in Example 1, using: 20 g of polyvinyl alcohol (Selvol 540 from Sekisui)

1 g of 3,4-dihydroxybenzaldehyde 1 g of N-methyl-4-(p-formylstyryl)pyridinium methyl sulfate 0.5 g of terephthaldehyde Solvent: water/isopropanol (200/50): 250 ml by first adding HCl and the SbQ, and maintaining the reaction mixture at 80° C. for 6 hours, followed by adding the terephthaldehyde. The formation of a hydrogel is observed.

The polymer obtained comprises 2.5% by weight (i.e. 0.8 mol %) of group derived from terephthaldehyde and 1% by weight (i.e. 0.98 mol %) of SbQ group derived from N-methyl-4-(p-formylstyryl)pyridinium methyl sulfate.

EXAMPLE 4 (Outside the Invention)

Polyvinyl Alcohol Polymer Functionalized with SbQ Groups (P4)

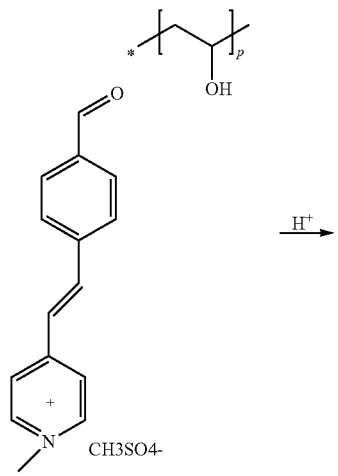

The polymer was prepared according to the procedure described in Example 1, using:

20 g of polyvinyl alcohol (Selvol 540 from Sekisui)

1 g of N-methyl-4-(p-formylstyryl)pyridinium methyl sulfate

Solvent: 200 ml of water

The polymer obtained comprises 15% by weight of SbQ group derived from N-methyl-4-(p-formylstyryl)pyridinium methyl sulfate.

EXAMPLE 5 (Outside the Invention)

Polyvinyl Alcohol Polymer Functionalized with SbQ Groups (P5)

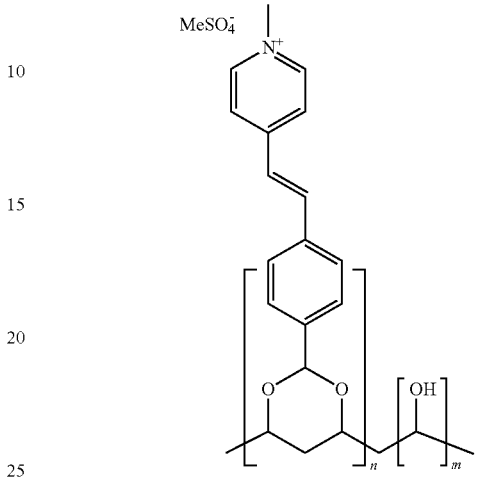

sold by the company Polysciences, Inc. under the catalogue reference 22570-75 with a degree of grafting with SbQ groups derived from N-methyl-4-(p-formylstyryl)pyridinium methyl sulfate of 4.1 mol %; molecular weight: ~45 000.

Comparative Examples 6 to 10

Evaluation of the Cosmetic Properties of the Polymers Applied to the Hair

The five compositions described below were prepared (weight percentages).

|  | Ex. 6 | Ex. 7 | Ex. 8* | Ex. 9* | Ex. 10* |
|---|---|---|---|---|---|
| Polymer 1 | 10 | | | | |
| Polymer 2 | | 10 | | | |
| Polymer 4 | | | 10 | | |
| Polymer 5 | | | | 10 | |
| PVA | | | | | 10 |
| Water | | | qs 100 | qs 100 | qs 100 |
| 50/50 water/isopropanol (weight/weight) | qs 100 | qs 100 | | | |

*examples outside the invention

A mixture of 40% by weight of bleaching powder sold under the name Platifiz® Precision by L'Oreal and 60% of aqueous hydrogen peroxide solution at 0.6% by weight was applied to locks of hair of curly type IV, in a bath ratio equal to 4, and the treated locks were then heated on a hotplate at 33° C. for 30 minutes. The locks were then rinsed with tap water and left to dry in a ventilated oven at 70° C. for one hour. This protocol was repeated a second time.

The polymer composition to be evaluated was applied to the locks thus bleached, using a brush, with a bath ratio equal to 1, on each side of the lock of hair. The lock was then exposed under a Sina UV Lamp & Dryer—56 W UV lamp for 6 minutes and was then dried on a hotplate at 50° C. for 15 minutes. The treated locks were then left at room temperature for 24 hours.

1 g of DOP camomile shampoo sold by La Scad was then applied per 2.8 g of locks, and the locks were massaged for 10 seconds, left to stand for three minutes and then rinsed with water at 37° C., 10 passes. The locks were then dried in a ventilated oven at 70° C. for 1 hour. Shampoo was applied five times in total.

The following cosmetic properties were then evaluated:

Feel: the feel by finger of the treated locks was evaluated by three people trained in sensory evaluation on hair, on softness tactile criteria.

Disentangling: disentangling using a comb was performed after immersing the lock for 10 seconds in water, with 5 passes of a small-toothed plastic comb (7 teeth/cm, tooth diameter of about 800 μm).

The evaluation was made in the following manner:
++: cosmetic property evaluated as effective
+: cosmetic property evaluated as moderately effective
0: cosmetic property evaluated as ineffective The following results were obtained:

| | Before shampooing | | | After 5 shampoo washes | | |
|---|---|---|---|---|---|---|
| Examples | Feel wet (softness) | Disentangling | Feel dry (softness) | Feel wet (softness) | Disentangling | Feel dry (softness) |
| 6 (P1) Invention | ++ | + | ++ | ++ | ++ | ++ |
| 7 (P2) Invention | ++ | + | ++ | ++ | + | ++ |
| 8* (P4) Comparative | + | 0 | + | 0 | 0 | 0 |
| 9* (P5) Comparative | + | 0 | + | 0 | 0 | 0 |
| 10* (PVA) Comparative | 0 | 0 | 0 | 0 | 0 | 0 |

It is seen from the results of the table that polymers P1 and P2 of the invention make it possible to improve the feel and the disentangling, before and even after five shampoo washes, versus PVA alone, or polymers P4 and P5 outside the invention which do not comprise hydrophobic chains.

The results obtained show that the polymers according to the invention give improved feel and disentangling properties.

EXAMPLE 11

The following composition is prepared (weight percentage):

| Polymer 3 (Example 3) | 6% |
|---|---|
| Water/isopropanol (50/50) | qs 100% |

The composition is applied to the hair and left to dry for 15 minutes at room temperature, and the hair is then exposed to light under a Sina UV Lamp & Dryer—56 W UV lamp for 6 minutes.

The hair thus treated has a soft feel and good disentangling, including after shampooing.

The invention claimed is:
1. A cosmetic process for treating keratin fibres, comprising:
(i) a step of applying to the keratin fibres a cosmetic composition comprising at least one polyvinyl alcohol polymer;
(ii) a step of irradiating the composition on the keratin fibres to crosslink said polymer;
steps (i) and (ii) being performed at the same time or in the order of step (i) followed by step (ii);
wherein the at least one polyvinyl alcohol polymer comprises:
a) at least one alcohol unit of formula (I)

b) optionally at least one acetate unit of formula (II)

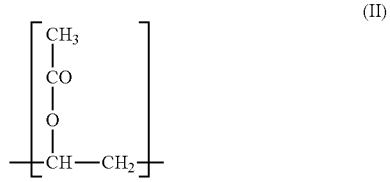

c) at least one photocrosslinkable unit of formula (P)

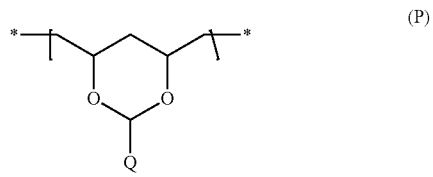

wherein * represents a bond that connects the part of the radical to the rest of the polymer, and wherein Q represents a styrylpyridinium group of formula (Q1) or (Q2) below:

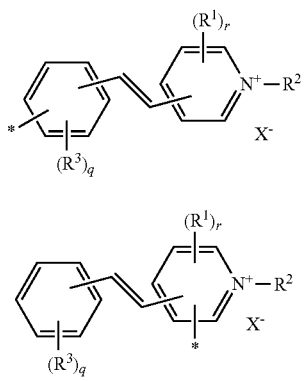
(Q1)

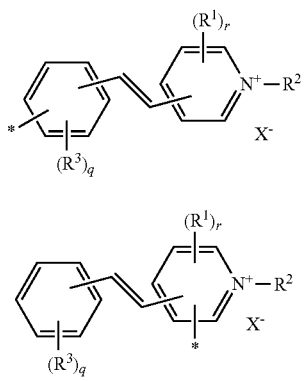
(Q2)

wherein $R^1$ and $R^3$, which may be identical or different, represent a halogen atom or a ($C_1$-$C_6$)alkyl group; or alternatively two contiguous groups $R^1$ or $R^3$ form, together with the carbon atoms that bear them, a benzo group;

$R^2$ represents a hydrogen atom, a ($C_1$-$C_6$)alkyl group optionally substituted with one or more halogen atoms or hydroxyl;

q and r represent an integer between 0 and 4 inclusive; and $X^-$ represents an anionic counterion chosen from halide ions, perchlorates, tetrafluoroborates, methylsulfate, phosphates, sulfates, methanesulfonates, or p-toluenesulfonate;

* represents a bond that connects the part of the radical to the rest of the polymer, d) and at least one hydrophobic unit of formula (H1) or (H2)

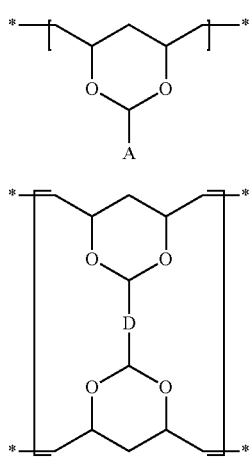
(H1)

(H2)

wherein:

* represents a bond that connects the part of the radical to the rest of the polymer, A represents a monovalent aromatic group of formula (A1) or (A2) below:

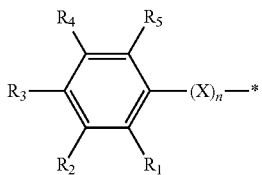
(A1)

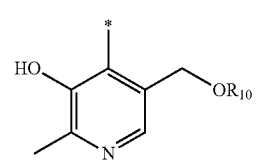
(A2)

wherein R1, R2, R3, R4, and R5, which may be identical or different, represent H, OH, ORa, SRa, $CO_2H$, —OCORb, —NRcRd, a C1-C4 alkyl radical optionally interrupted with one or more heteroatoms O or S, or a divalent group N(Re), Ra representing a C1-C6 alkyl group;
Rb representing a C1-C6 alkyl or benzyl group;
Rc and Re representing a C1-C4 alkyl group;
Rd representing H or a C1-C4 alkyl group;
* represents a bond that connects the part of the radical to the rest of the polymer;
n=0 or 1; wherein when n=0, then R1, R2, R3 and R4 do not all represent a hydrogen atom;
X represents a divalent radical —CH=C(Rf)—;
Rf represents H or a C1-C6 alkyl radical;
$R_{10}$ represents H or a phosphate group —PO(OH)$_2$,
D represents a divalent group of formula (D1) or (D2) below:

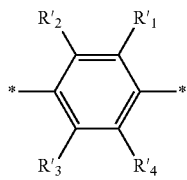
(D1)

wherein R'1, R'2, R'3 and R'4, which may be identical or different, represent H, a C1-C4 alkyl radical, or a C1-C4 alkoxy radical,

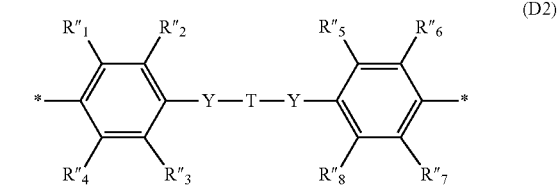
(D2)

wherein R"1, R"2, R"3, R"4, R"5, R"6, R"7, and R"8, which may be identical or different, represent H, a C1-C4 alkyl radical or a C1-C4 alkoxy radical;

Y represents O or —N(Rj)—,
Rj represents a C1-C4 alkyl group; and
T represents a divalent hydrocarbon-based group containing from 2 to 6 carbon atoms.

2. The process according to claim 1, wherein the polymer contains at least one hydrophobic unit of formula (H1), wherein the hydrophobic unit of formula (H1) contains a group of formula (A1) chosen from formulas (1)-(29):
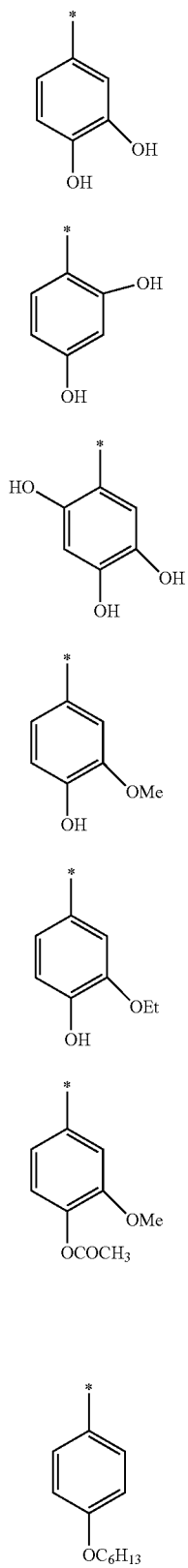
-continued
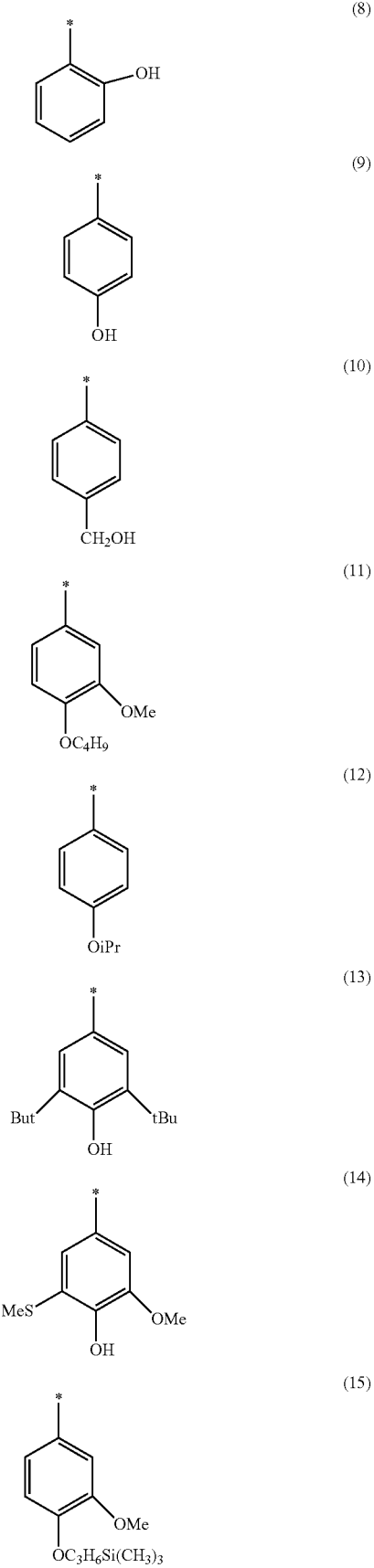

-continued
(16) 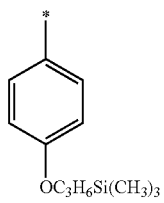
(17) 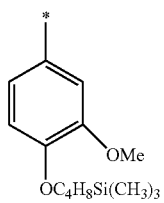
(18) 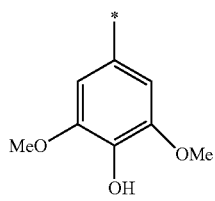
(19) 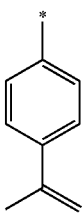
(20) 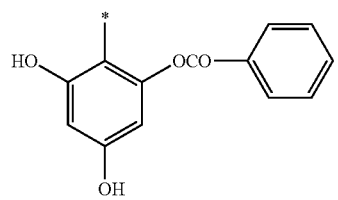
(21) 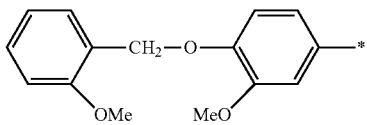
(22) 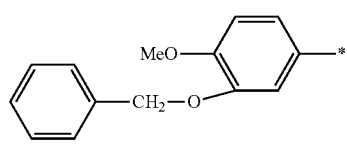
(23) 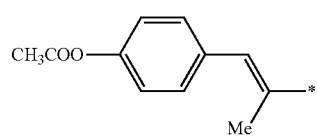
(24) 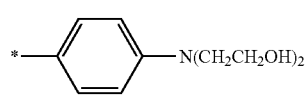
-continued
(25) 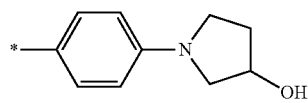
(26) 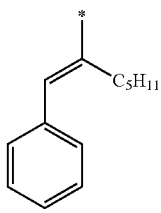
(27) 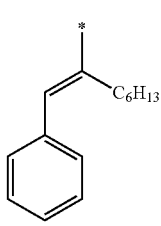
(28) 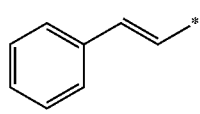
(29) 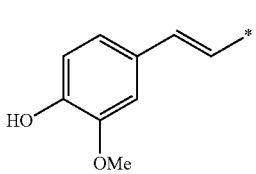
wherein * represents a bond that connects the part of the radical to the rest of the polymer.
3. The process according to claim 1, wherein the polymer contains at least one hydrophobic unit of formula (H2), wherein the hydrophobic unit of formula (H2) contains:
a) a group of formula (D1) chosen from formulas (32)-(34):
(32) 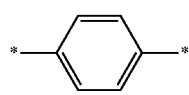
(33) 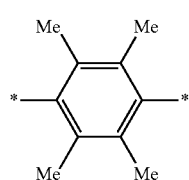
(34) 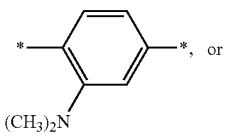, or b) a group of formula (D2) chosen from formulas (35)-(36):

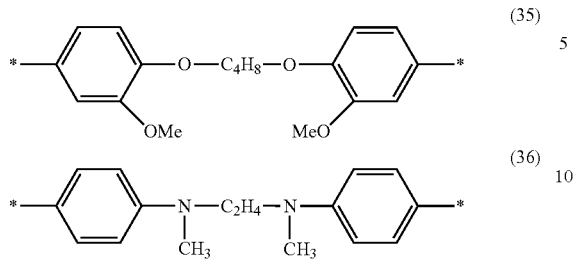

wherein * represents a bond that connects the part of the radical to the rest of the polymer.

4. The process according to claim 1, wherein the group Q of the unit (P) represents the group:

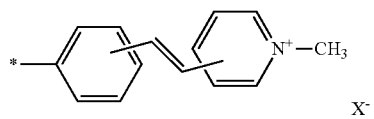

wherein $X^-$ represents an anionic counterion chosen from halide ions, perchlorates, tetrafluoroborates, methylsulfate, phosphate, sulfate, methanesulfonates or p-toluenesulfonate.

5. The process according to claim 1, wherein the polymer comprises at least one unit of formula (II) present in the polyvinyl alcohol in an amount ranging from 0.1 mol % to 40 mol % relative to the polymer.

6. The process according to claim 1, wherein the polymer comprises a photocrosslinkable unit (P) in an amount ranging from 0.2 mol % to 10 mol % relative to the polymer.

7. The process according to claim 1, wherein the polymer comprises a hydrophobic unit (H1) and/or (H2) in an amount ranging from 0.2 mol % to 50 mol % relative to the polymer.

8. The process according to claim 1, wherein said polymer has a weight-average molecular weight ranging from 10,000 to 200,000 g/mol.

9. The process according to claim 1, wherein the polymer is present in the cosmetic composition in an amount ranging from 0.1% to 40% by weight, relative to the total weight of the composition.

10. The process according to claim 1, wherein the irradiation is irradiation with radiation in the UVA domain.

11. The process according to claim 1, wherein the keratin fibers are damaged and/or sensitized hair, and the process is a process for improving at least one property of the hair chosen from feel and/or ease of detangling, and the improvement in feel and/or ease of detangling persists through at least one shampoo wash.

12. A process for improving at least one property of hair chosen from feel and/or ease of detangling, comprising:
(i) a step of applying to the hair a cosmetic composition comprising at least one polyvinyl alcohol polymer comprising:
a) at least one alcohol unit of formula (I):

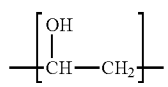

b) optionally at least one acetate unit of formula (II):

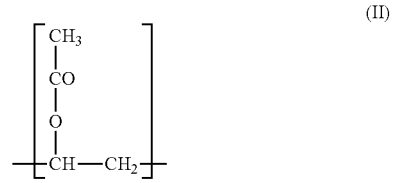

c) at least one photocrosslinkable unit of formula (P):

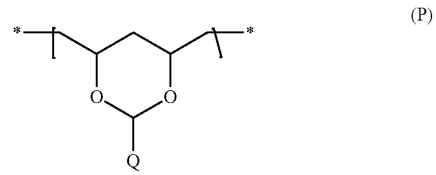

wherein * represents a bond that connects the part of the radical to the rest of the polymer, and wherein Q represents a styrylpyridinium group of formula (Q1) or (Q2) below:

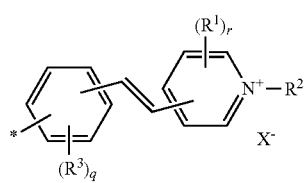

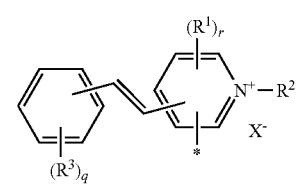

wherein:
R1 and R3, which may be identical or different, represent a halogen atom or a $(C_1$-$C_6)$alkyl group; or alternatively two contiguous groups $R^1$ or $R^3$ form, together with the carbon atoms that bear them, a benzo group;

$R^2$ represents a hydrogen atom, a $(C_1$-$C_6)$alkyl group optionally substituted with one or more halogen atoms or hydroxyl;

q and r independently represent an integer between 0 and 4 inclusive;

$X^-$ represents an anionic counterion chosen from halide ions, perchlorates, tetrafluoroborates, methylsulfate, phosphates, sulfates, methanesulfonates, or p-toluenesulfonate; and

* represents a bond that connects the part of the radical to the rest of the polymer, and d) at least one hydrophobic unit of formula (H1) or (H2):

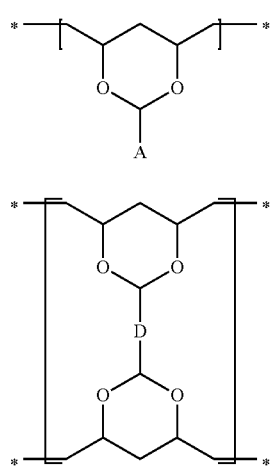

wherein:

* represents a bond that connects the part of the radical to the rest of the polymer, A represents a monovalent aromatic group of formula (A1) or (A2) below:

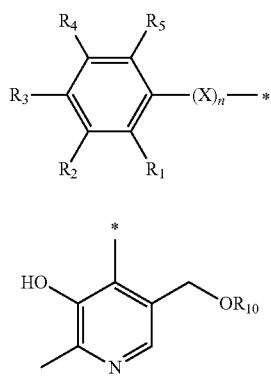

wherein R1, R2, R3, R4, and R5, which may be identical or different, represent H, OH, ORa, SRa, $CO_2H$, —OCORb, —NRcRd, a C1-C4 alkyl radical optionally interrupted with one or more heteroatoms O or S, or a divalent group N(Re), with Ra representing a C1-C6 alkyl group;

Rb representing a C1-C6 alkyl or benzyl group;

Rc and Re independently representing a C1-C4 alkyl group;

Rd representing H or a C1-C4 alkyl group;

* representing a bond that connects the part of the radical to the rest of the polymer;

n=0 or 1; wherein when n=0, then R1, R2, R3 and R4 do not all represent a hydrogen atom;

X representing a divalent radical —CH=C(Rf)—;

Rf representing H or a C1-C6 alkyl radical;

$R_{10}$ representing H or a phosphate group —$PO(OH)_2$,

D represents a divalent group of formula (D1) or (D2) below:

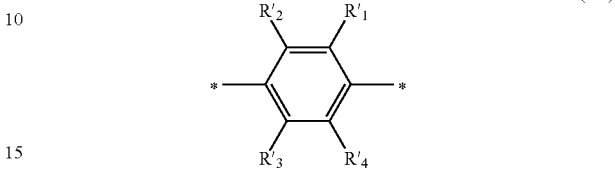

wherein R'1, R'2, R'3 and R'4, which may be identical or different, represent H, a C1-C4 alkyl radical, or a C1-C4 alkoxy radical,

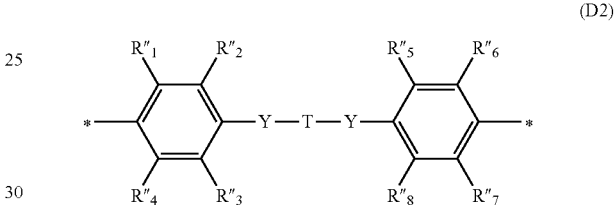

wherein R"1, R"2, R"3, R"4, R"5, R"6, R"7, and R"8, which may be identical or different, represent H, a C1-C4 alkyl radical or a C1-C4 alkoxy radical; with Y representing O or —N(Rj)—, Rj representing a C1-C4 alkyl group; and T representing a divalent hydrocarbon-based group containing from 2 to 6 carbon atoms; and (ii) a step of irradiating the composition on the hair to crosslink at least two photocrosslinkable units of formula (P);

steps (i) and (ii) being performed at the same time or in the order of step (i) followed by step (ii).

13. The process according to claim 12, wherein the hair to which the composition is applied is damaged and/or sensitized hair.

14. The process according to claim 12, wherein an improvement in feel and/or ease of disentangling persists through at least one shampoo wash.

15. The process according to claim 12, wherein an improvement in feel and/or ease of disentangling persists through at least five shampoo washes.

16. The process according to claim 12, wherein the process is performed during or after a process for shaping, dyeing, and/or bleaching the hair.

17. The process according to claim 12, wherein the polymer is present in the cosmetic composition in an amount ranging from 0.1% to 40% by weight, relative to the total weight of the composition.

18. The process according to claim 12, wherein the cosmetic composition comprises at least one polyvinyl alcohol polymer of formulae (X), (Y), and/or (Z):

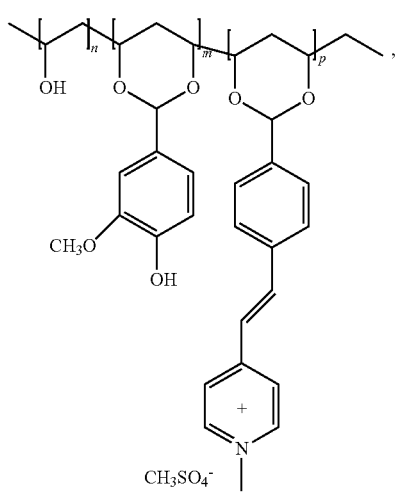

(X)

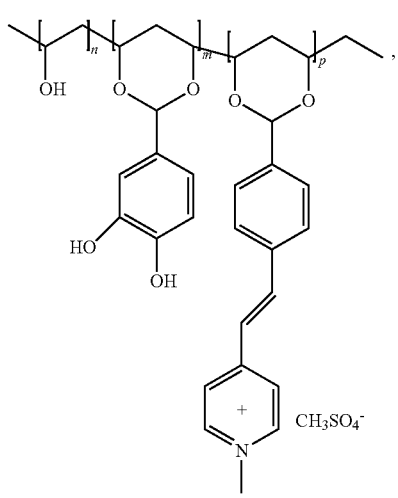

(Y)

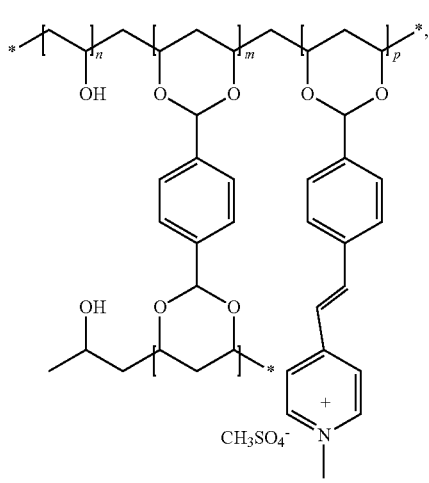

(Z)

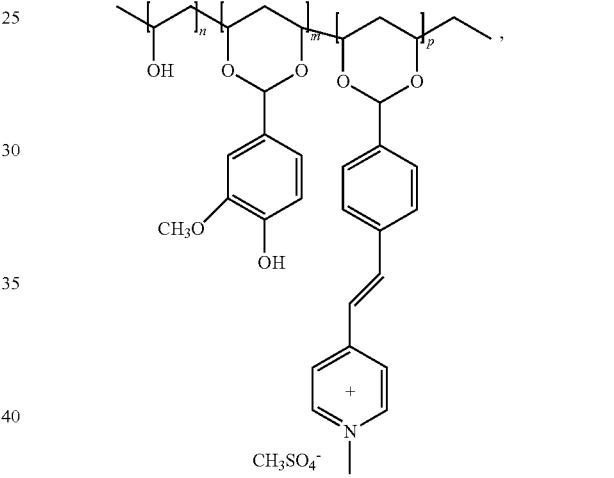

(X)

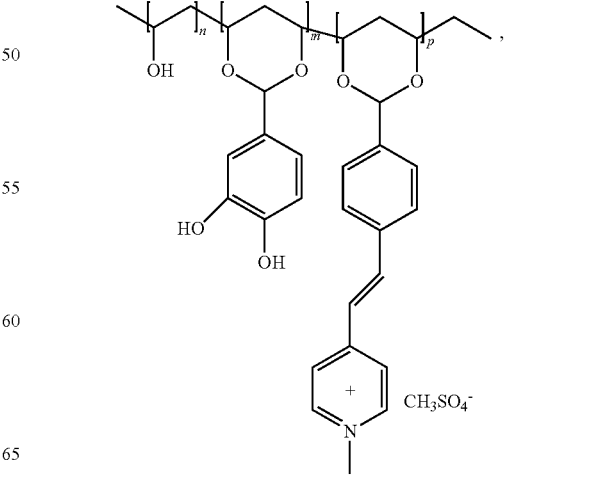

(Y)

wherein in formulae (X), (Y), and (Z):
n is an integer chosen such that the polymer comprises from 0.1 mol % to 40 mol % of n units relative to the total polymer;
m is an integer chosen such that the polymer comprises from 0.2 mol % to 50 mol % of m units relative to the total polymer; and
p is an integer chosen such that the polymer comprises from 0.2 mol % to 10 mol % of p units relative to the total polymer.

19. The process according to claim 12, wherein the irradiation is irradiation with radiation in the UVA domain.

20. A process for improving at least one property of hair chosen from feel and/or ease of detangling, comprising:
(i) a step of applying to the hair a cosmetic composition comprising from 1% to 10% of at least one polyvinyl alcohol polymer of formulae (X), (Y), and/or (Z) in an aqueous medium:

-continued

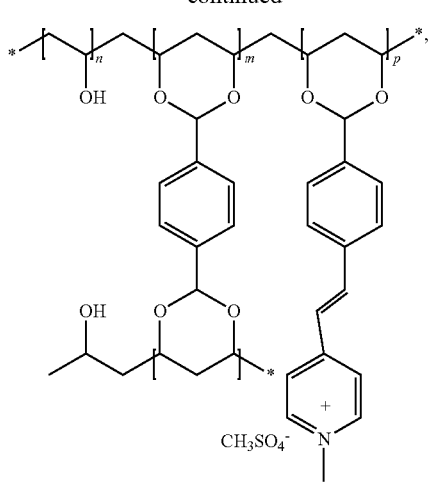
(Z)

wherein in formulae (X), (Y), and (Z):

n is an integer chosen such that the polymer comprises from 0.1 mol % to 40 mol % of n units relative to the total polymer;

m is an integer chosen such that the polymer comprises from 0.2 mol % to 50 mol % of m units relative to the total polymer; and p is an integer chosen such that the polymer comprises from 0.2 mol % to 10 mol % of p units relative to the total polymer, and (ii) a step of irradiating the composition on the hair with radiation in the UVA domain to crosslink the polymer;

steps (i) and (ii) being performed at the same time or in the order of step (i) followed by step (ii).

* * * * *